United States Patent [19]
Segerdal

[11] Patent Number: 5,441,410
[45] Date of Patent: Aug. 15, 1995

[54] DISPOSABLE SALIVA EJECTOR

[76] Inventor: Michael J. Segerdal, 4643 Alveo Rd., LaCanada, Calif. 91011

[21] Appl. No.: 39,162
[22] PCT Filed: Apr. 13, 1992
[86] PCT No.: PCT/US92/02986
  § 371 Date: Apr. 8, 1993
  § 102(e) Date: Apr. 8, 1993
[87] PCT Pub. No.: WO93/20776
  PCT Pub. Date: Oct. 28, 1993
[51] Int. Cl.$^6$ ............................................. A61C 17/06
[52] U.S. Cl. ........................................ 433/93; 433/95; 433/96
[58] Field of Search ............... 433/91, 92, 93, 94, 433/95, 96; 604/902, 119

[56] References Cited
U.S. PATENT DOCUMENTS

| | | | |
|---|---|---|---|
| 1,447,020 | 2/1923 | Grunberg | 433/91 |
| 2,637,106 | 5/1953 | Otis | 433/91 |
| 4,227,529 | 10/1980 | Lomholt | 433/96 |
| 4,265,621 | 5/1981 | McVey | 433/91 |
| 4,878,900 | 11/1989 | Sundt | 433/91 |
| 5,066,228 | 11/1991 | Doundoulakis et al. | 433/91 |
| 5,078,603 | 1/1992 | Cohen | 433/91 |
| 5,080,587 | 1/1992 | Miyao | 433/91 |

Primary Examiner—Cary E. O'Connor
Attorney, Agent, or Firm—Albert O. Cota

[57] ABSTRACT

A disposable saliva ejector which has a formable hollow tube (40) with a tip (42) on the end with openings for drawing in saliva. The tube has a beveled hole (46) near the top through which single-integral instruments such as a scaler or a rotary instrument such as a polishing brush may be cleaned of debris and the hole may be varied in size by bending outwardly or inwardly. A finger over the hole also may vary suction within the tube for manual volume control. The tip includes a guard (48) of a flat and resilient material preventing tissue aspiration into openings in the tip. Waste materials are trapped inside the tube with teeth (58), fingers (6) or shelves (62) that project inwardly. Debris may also be trapped by a loop (66) or S-shaped bend (68) in the tube itself. The ejector is disposed of after use on singular patient.

19 Claims, 4 Drawing Sheets

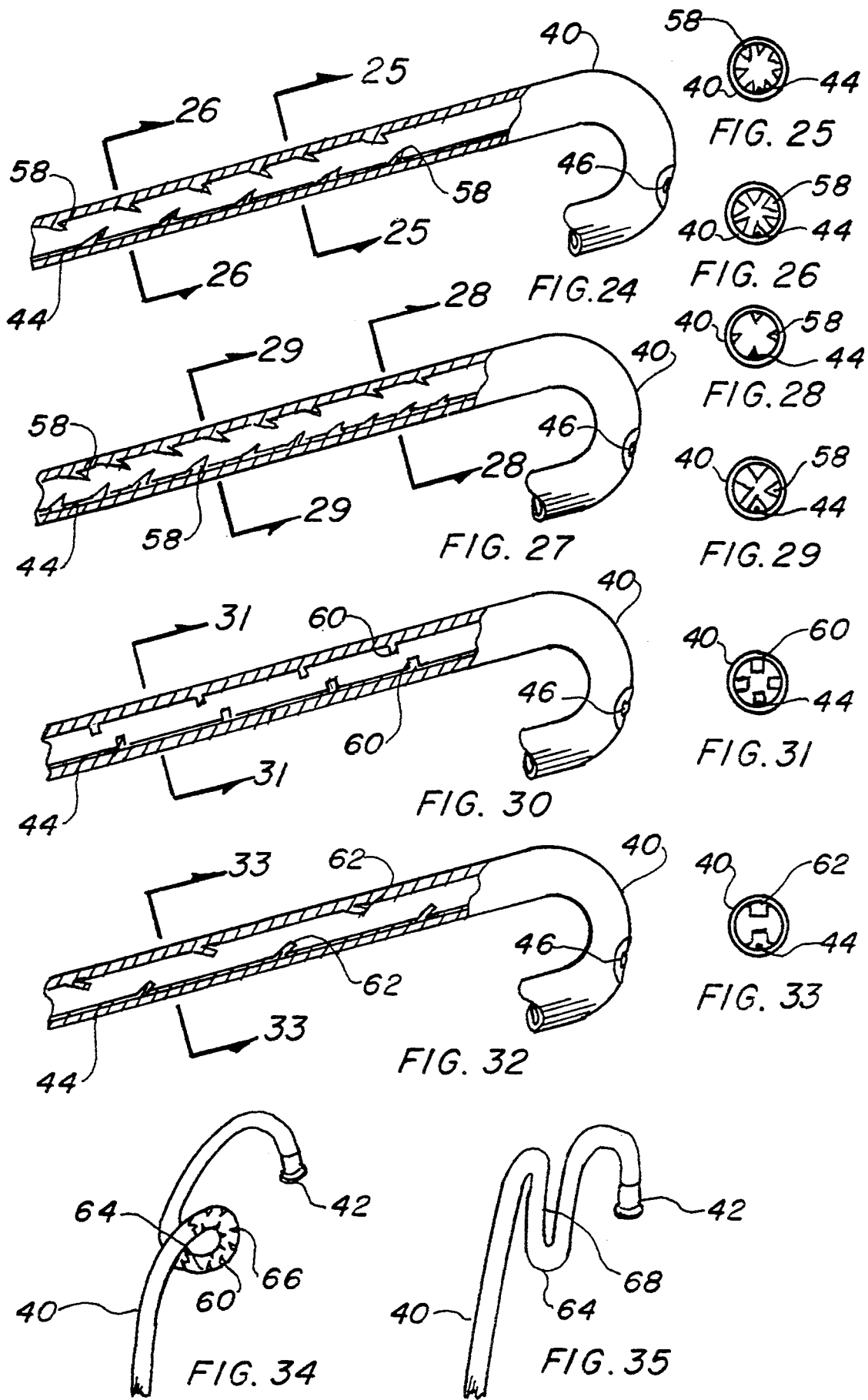

DISPOSABLE SALIVA EJECTOR

TECHNICAL FIELD

The present invention relates to saliva ejectors in general. More specifically to an ejector that is regulatable in negative pressure and flow, protects oral tissue and collects debris inside during use and is disposable thereafter.

BACKGROUND ART

Previously, many types of saliva ejectors have been used in endeavoring to provide an effective means for removing saliva from a patient's mouth during dental treatment.

Previously this device for saliva removal has been limited to screens and the like for separating and isolating matter that is in the mouth created by the type of dental work being completed. Further valves and manually covered holes in the body of the ejector have been used to regulate flow and vacuum from the device and the tip of the ejector is hard and of the same basic material.

A search of the prior art did not disclose any patents that read directly on the claims of the instant invention, however the following U.S. patents are considered related:

| U.S. PAT. NO. | INVENTOR | ISSUED |
| --- | --- | --- |
| 5,076,787 | Overmyer | 31 December 1991 |
| 4,221,220 | Hansen | 9 September 1980 |
| 3,453,735 | Burt | 8 July 1969 |
| 1,222,267 | Cosad | 10 April 1917 |
| 602,572 | Browne, et al | 19 April 1898 |

Overmyer in U.S. Pat. No. 5,076,787 discloses a variable suction aspirator head with a solid trap that regulates suction by positioning a slidable outer barrel over a valve tube that contains a number of slotted holes. The device is dissembled for cleaning and sterilization after each use.

U.S. Pat. No. 4,221,220 issued to Hansen teaches a surgical suction nozzle for removing debris from unconscious patients. The suction tip contains a raised ridge inward of the opening in the end. A suction control hole is located in the medial segment of the nozzle allowing control of the amount of suction by placing a finger over the hole during use.

Burt employs a rectangular passage for controlling the amount of suction in the dental aspirator in U.S. Pat. No. 3,453,735. The tip has a two plane surface at different angular relations to the axis of the deflected portion to prevent drawing tissue into the outer end of the tube. The operator places a finger on the passage to obtain the desired negative pressure.

Although the prior art on aspirators has been referred to, it should be pointed out that in dentistry, an aspirator tip and a saliva ejector are two different instruments. The saliva ejector, up until now, being a passage non-operated instrument that usually rests passively in the mouth, drawing away saliva. By contrast, the aspirator tip is an active instrument, which is operated by an assistant while the dentist/oral-surgeon works, and the assistant maintains a clear field of work, by moving the aspirator tip as needed, to areas of debris, such as removal of large amalgam filings, or relatively large amounts of blood, which might otherwise obscure the operating site.

U.S. Pat. No. 1,222,267 of Cosad employs air vents and fluid passages to prevent tissue damage. Two passageways extend almost the length of the device allowing a counter current of air to be passed therethrough. Although a hole is used for airflow, the dental practitioner does not cover the hole in use.

A patent issued before the turn of the century to Browne et al, U.S. Pat. No. 602,522 discloses a glass tube with a strainer and a chamber. The principle of using a tube for ejecting saliva is obviously well known and the tip employs at least two openings one on the end and the other on the side.

As the prior art indicated, the use of U-shaped tube with some types of tip is not by itself novel. Also, a hole in the side for manual volume control has been used previously however, only simple strainers have been employed for retaining debris and the tips are not resilient on the ends. Further, the hole or passage in the side has been limited to just an opening not large enough or configured to clean tools or close and change its shape for regulation of volume.

DISCLOSURE OF THE INVENTION

The conventional use of saliva ejectors has not changed for almost a century however, as dentistry has become more sophisticated and time to accomplish a given task is of a premium, improvements in creating time saving and safer equipment and methods is long overdue in this art.

It is therefore a primary object of the invention to utilize a novel shaped beveled hole in the formable tube of the ejector positioned near the bent shape that is located within the patient's oral cavity when in use. This beveled hole which can be cut in any shape acts as a receptacle to dispose of debris and tartar from the end of a single-integral instrument being used such as a scaler. The dental practitioner instead of reaching for a gauze on the bracket table simply places the tip of the instrument in the hole and the high velocity suction at the opening pulls the matter off of the end into the interior of the tube in the main airstream. Further, the shape allows a scraping action to be used in the event the waste material is hard to release form the instrument tip. Furthermore, it is possible to remove splatter from a prophy angle by running the cup, with the splatter accumulated, down the side of the ejector with the substance such as copious paste evacuated into the hole before the agglomeration flies off the rotating cup.

The beveled hole also enables various rotary instruments, such as polishing brushes, discs, burs, to be wiped across the hole, removing splatter, blood, or other debris. Also, by passing the reflecting side of the mouth mirror across the hole, vision-interfering water droplets or particles may be quickly sucked off the mouth mirror, saving labor or longer interruption of the procedure.

It may easily be seen that an important object is the time savings involved which is obvious as an assistant does not have to stand by wiping the instrument and consequently the time spent to physically wipe the instruments by hand is completely eliminated. While cleaning an instrument by itself is easy and does not on the surface appear to be that important, the procedure must be accomplished numerous times and the accumulation of even short durations can become a major overall time saving procedure.

Furthermore, another object of the invention precludes infecting the dental practitioner or dental assistant by the accidentally pricking of a finger or hand with a sharp instrument that contains traces of blood and other microorganisms. With the danger of blood transmitted diseases now prevalent in our society, this object is very real and the common procedure of wiping an instrument with a gauze subjects the user to this type of mishap even when wearing rubber gloves.

Still another object of the invention is directed to the ability of the device to be adjusted in suction pressure. This adjustment is easily accomplished by either placing one's finger on the beveled hole to permit the entire flow to be realized from the tip for short durations or to bend the ejector tube. The suction can also be adjusted by the operator turning a rotary valve attached to the end of the main hose at the point where the saliva ejector is located, this action can create more cross-contamination. Further, the beveled hole in its open position draws airborne bacteria into the tube from the patient's mouth to the degree of the opening deforming the hole thereby reducing the hole-area, acting as a manual control valve, and hence permitting more flow from the tip.

Yet another object of the invention prevents tissue aspiration in the patient's oral cavity. Mucous membrane and other soft tissues are subject to potential trauma when drawn into the openings of the ejector tip. This action as well as causing immediate pain may lead to sores, blisters, or cankers in the patient's mouth which is not conducive for good patient to dentist relationships. The invention prevents this problem by using a tip guard on the extending end of the ejector. The guard consists of either a flat pad of semirigid material, the same as used on the tip, or a resilient pad which may consist of an air cushion or a closed cell sponge or the like. In any case, the guard is larger in diameter than the balance of the tip placing the slots in the tip away from the periphery of the pad such that any angle or even when juxtapositioned parallel with the patient's mouth or tongue, no tissue aspiration will occur.

A further object of the invention is the ability of the tube itself to become a filter and retain the debris inside the tube. The usual function of an ejector is to transmit into the main tube all types of material such as tartar, excess filings, small blood clots, pieces of retraction cord impression materials and the like. The invention has the capabilities of reducing much of this problem in that small teeth or finger like structures project inwardly from the internal wall of the ejector formable tube in various embodiments, trapping debris from the smallest pieces separable from the air stream to the large pieces most of which are caught and retained in the tube interior. When finished with each patient the ejector is disconnected from the vacuum hose and discarded with the user handling only the outside surface of the tube.

The cost of the ejector with the improvements described above is equal to or not much greater than those presently in use therefore, the advantage of utility far overcomes the disadvantage of a slight increase in cost.

These and other objects and advantages of the present invention will become apparent from the subsequent detailed description of the preferred embodiment and the claims taken in conjunction with the accompanying drawings.

BRIEF DESCRIPTION OF THE DRAWINGS

FIG. 24 is a fragmentary side view of the invention partially cut away on the centerline to show the embodiment of the debris retaining means having inwardly facing teeth.

FIG. 25 is a cross sectional view taken along lines 25—25 of FIG. 24.

FIG. 26 is a cross sectional view taken along lines 26—26 of FIG. 24.

FIG. 27 is a fragmentary side view of the invention partially cut away on the centerline to show the embodiment of the debris retaining means having progressively larger inwardly facing teeth.

FIG. 28 is a cross sectional view taken along lines 28—28 of FIG. 27.

FIG. 29 is a cross sectional view taken along lines 29—29 of FIG. 27.

FIG. 30 is a fragmentary side view of the invention partially cut away on the centerline to show the embodiment of the debris retaining means having inwardly facing fingers.

FIG. 31 is a cross sectional view taken along lines 31—31 of FIG. 30.

FIG. 32 is a fragmentary side view of the invention partially cut away on the centerline to show the embodiment of the debris retaining means having inwardly facing shelves.

FIG. 33 is a cross sectional view taken along lines 33—33 of FIG. 32.

FIG. 34 is a side view of the invention bent in a loop to form a trap.

FIG. 35 is a side view of the invention bent in a S-shape to form a trap.

BEST MODE FOR CARRYING OUT THE INVENTION

Figure 6:
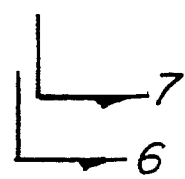
FIG. 6 is a cross sectional view taken along lines 6—6 of FIG. 4.

The best mode for carrying out the invention is presented in terms of a preferred embodiment. The preferred embodiment, as shown in FIGS. 1 through 35 is comprised of a formable hollow tube 40 that has a tip 42 on one end. The tube 40 by itself is well known in the art and is made with a wire 44 inside, shown in FIGS. 6 and 7 which holds the tube in the desired shape when manually bent. The tube 40 is connected to a vacuum pump on the end opposite the tip 42 by a flexible hose and the tip is placed on the patient's mouth to withdraw saliva during dental procedures.

Figure 4:
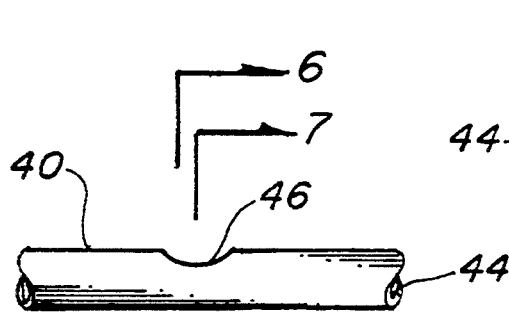
FIG. 4 is a side view of the formable tube illustrating the beveled hole.
Figure 5:
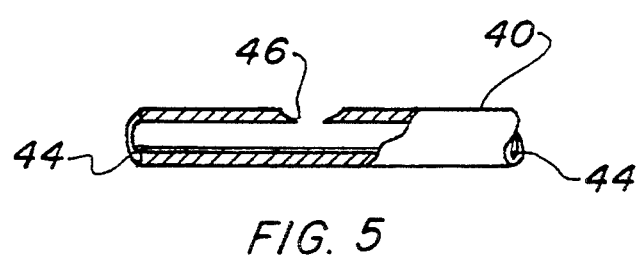
FIG. 5 is a side fragmentary view of the tube partially cut away to show the hole.
Figure 7:
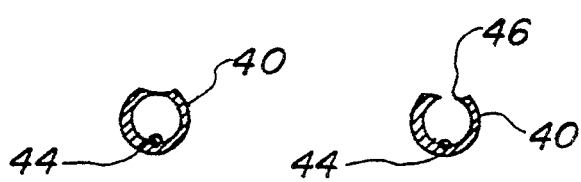
FIG. 7 is a cross sectional view taken along lines 7—7 of FIG. 4.
Figures 8, 9:
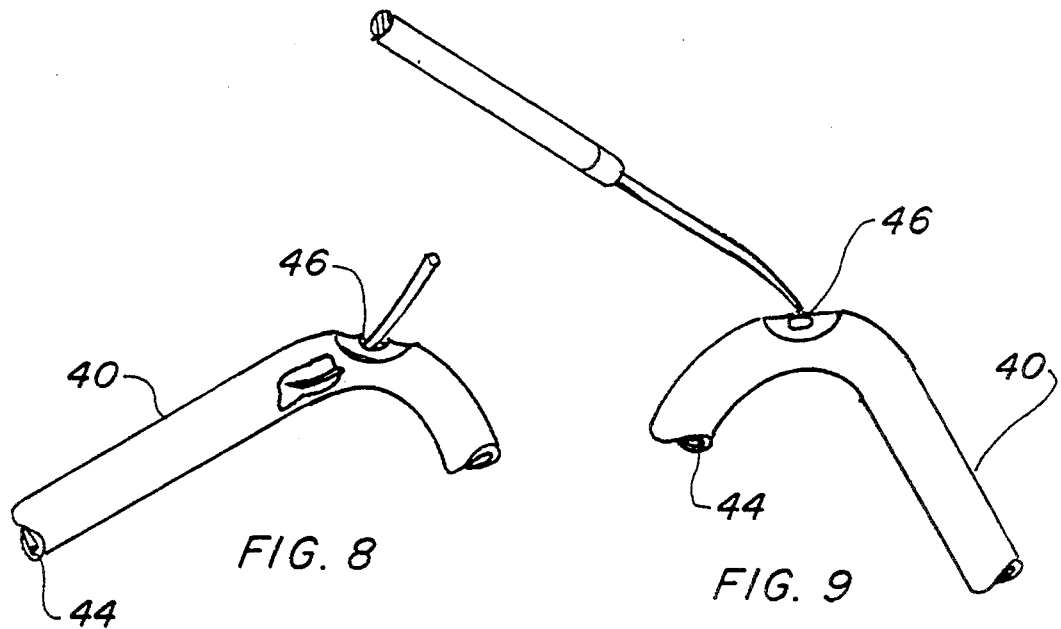
FIG. 8 is a partial isometric view of the tube with an instrument penetrating the hole to clean debris therefrom.
FIG. 9 is a partial isometric view of the tube with an instrument above the hole with the vacuum pulling off debris therefrom.
Figures 10, 11:
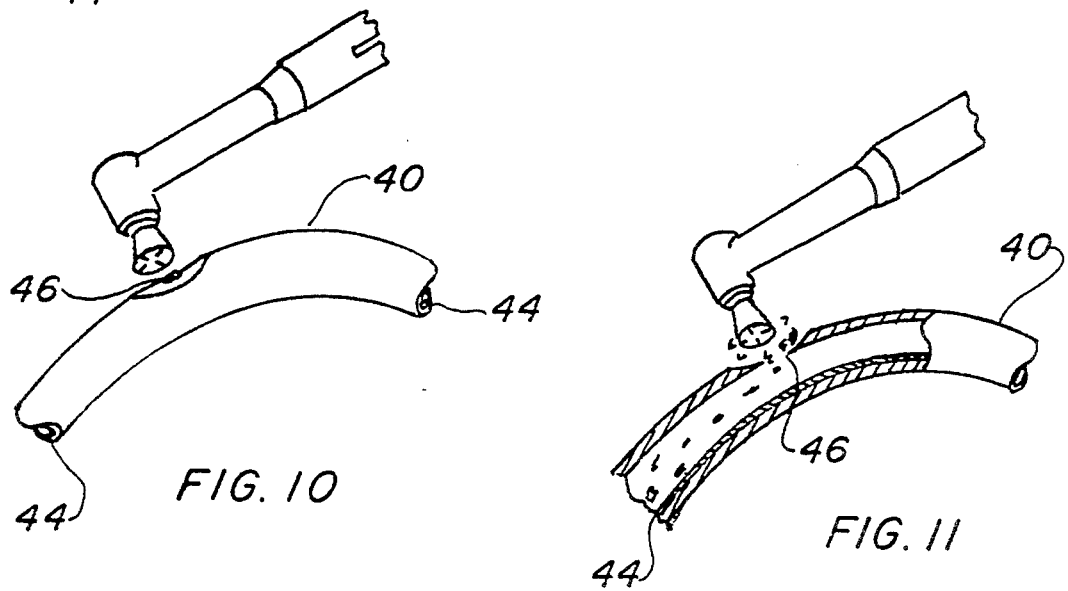
FIG. 10 is a partial isometric view of the tube with splatter being removed through the hole from a prophy angle.
FIG. 11 is the same as FIG. 10 except the tube is shown cut on the centerline illustrating the debris inside.
Figures 12, 13, 14:
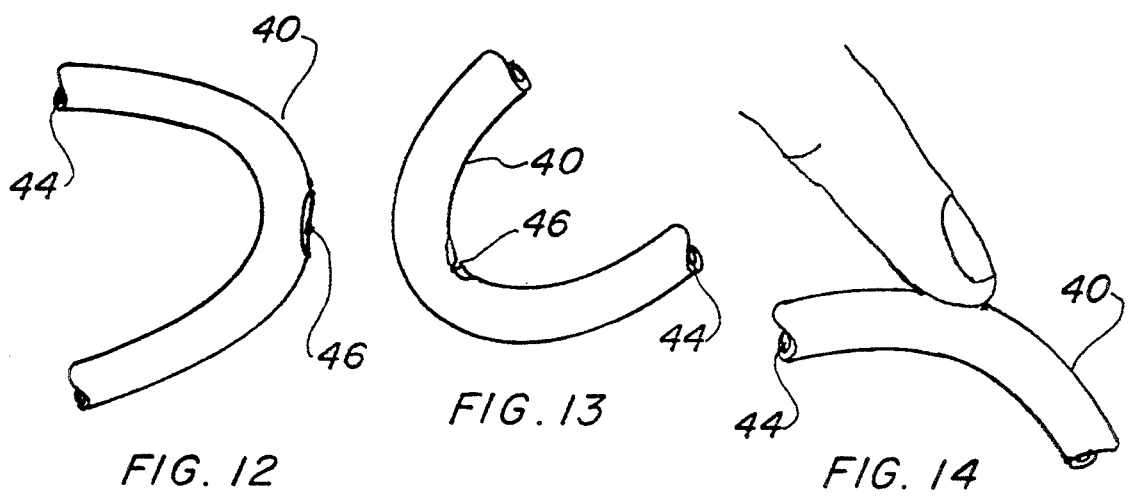
FIG. 12 is a side view of the tube bent outwardly.
FIG. 13 is a side view of the tube bent inwardly.
FIG. 14 is a side view of an operator's finger shown covering the hole for volume control.

The tube 40 contains a beveled hole 46 serving a dual purpose, which is, to regulate the volume of the vacuum and also for cleaning debris from tools through the hole 46. The hole 46 itself is shaped like a concave dish with the hole penetrating the tube at a sharp angle as illustrated in FIGS. 4 and 7. The shape of the hole 42 permits a tool to be inserted without binding and is the proper shape for the dentist or other members of the staff to place a finger over the hole for vacuum regulation. This procedure is illustrated in FIG. 14. The hole 42 preferably has a diameter of from 2 to 4 millimeters when the tube 40 is straight and becomes oval in shape when the tube is bent in an arc, such as depicted in FIG. 12. In FIG. 13, the hole actually reduces in size until it is entirely pinched closed according to the tightness of the bend. This variable closure becomes the regulation for controlling the volume of flow and negative pressure characteristics within the tube. Preferably, the hole 46 is from 9 to 35 millimeters from the tip 42 to the hole center which in practice provides a convenient location inside the patient's mouth when in use.

Figure 15:
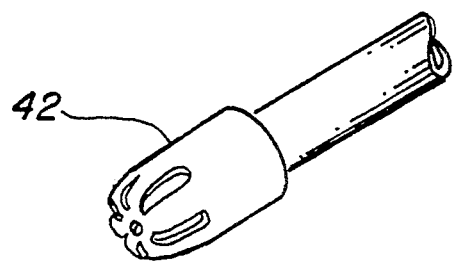
FIG. 15 is a partial isometric view of a tip as used in prior art.
Figure 16:
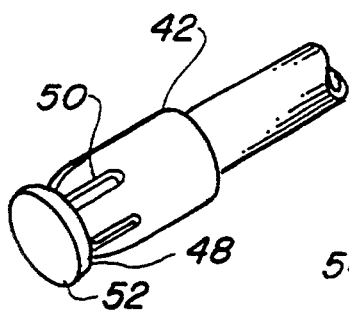
FIG. 16 is a partial isometric view of the embodiment of the tip installed on the outside having a flat pad.
Figure 17:
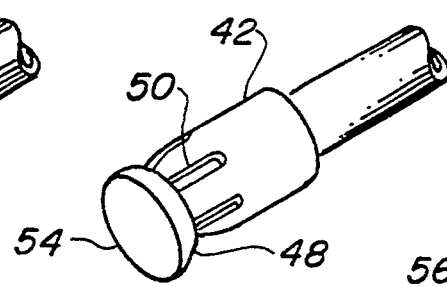
FIG. 17 is a partial isometric view of the embodiment of the tip installed on the outside having an air cushion on the pad.
Figure 18:
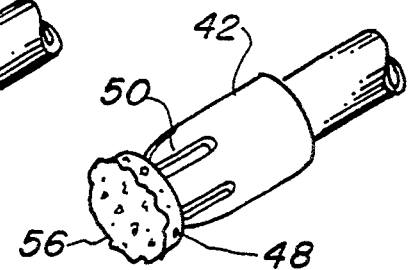
FIG. 18 is a partial isometric view of the embodiment of the tip installed on the outside having a sponge on the pad.
Figure 19:
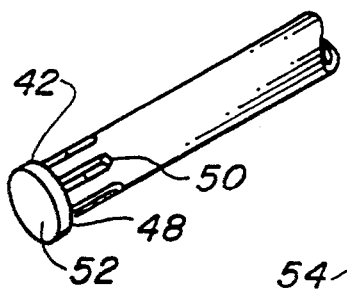
FIG. 19 is a partial isometric view of the embodiment of the tip installed on the inside having a flat pad.
Figure 20:
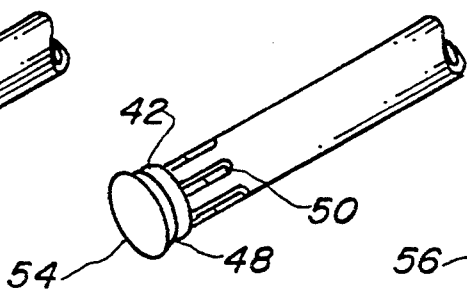
FIG. 20 is a partial isometric view of the embodiment of the tip installed on the inside having an air cushion on the pad.
Figure 21:
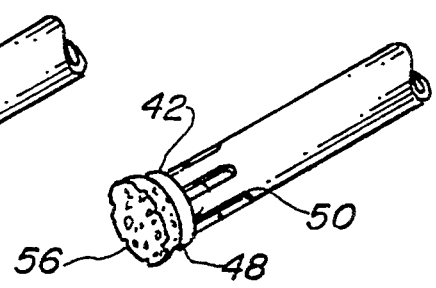
FIG. 21 is a partial isometric view of the embodiment of the tip installed on the inside having a sponge on the pad.
Figure 22:
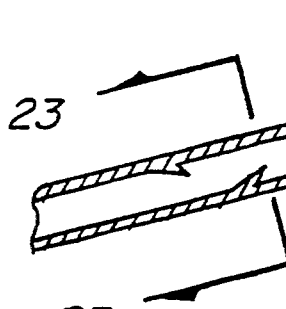
FIG. 22 is a partial isometric view of the invention with the tube cut away to illustrate the retaining means inside.
Figure 23:
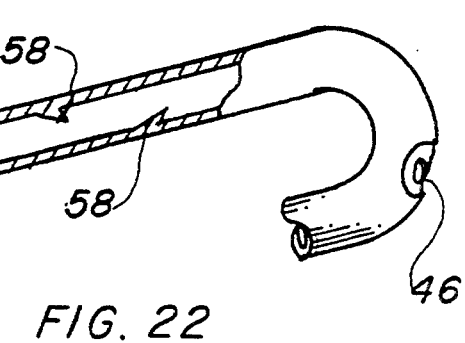
FIG. 23 is a cross sectional view taken along lines 23—23 of FIG. 22.
Figure 23:
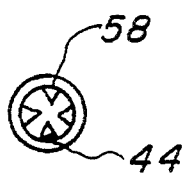

The tip 42 of the invention is modified from the prior art shown in FIG. 15 as it contains an integral tip guard 48 on the distal end to prevent tissue aspiration from the patient into the slotted openings 50 in the tip. Basically, all embodiments of the tip guard 48 have a flat pad 52 incorporated into the end as shown in FIGS. 16 through 19 formed integrally and of the same material as the guard. It will be noted however, that no openings are present and the diameter is larger than the tip itself preventing aspiration when the tip 42 is laid flat in the patient's mouth. Another embodiment is illustrated in FIGS. 17 and 20 wherein a soft material such as an air cushion 54 is integrally formed on the distal end of the pad 52. This makes the end pliable and soft furthering the utility of the improvement. The same features may be realized by the use of a closed cell sponge 56 depicted in FIGS. 18 and 21. In either event, the softness provides comfort to the patient as the disadvantage of the hard tip of prior art is apparent. The tip 42 itself with its improvements may be attached either over or within the tube 40. The method of attachment is illustrated in FIGS. 16–18 which is over or outside of the tube whereas FIGS. 19–21 slip the tip 42 inside or into the tube in any event, the tip is sized to be retained by a interference fit or with the use of a bonding agent such as an adhesive. Alternatively, the slotted openings 50 can be cut directly into the end of the tube (not shown).

The invention includes, as one of the most important elements, debris retaining means within the tube 40, positioned in such a manner as to catch and hold debris namely, tartar and other waste materials present in the patient's mouth during dental procedures. Materials can be retained inside the tube and disposal of the entire ejector after use on a singular patient is then accomplished.

The first embodiment of the retaining means is illustrated in FIGS. 22–26 and consists of a number of triangular shaped teeth 58 positioned at intervals inside the tube 40 facing inwardly forming traps by the very nature of their shape. The larger size debris is retained by opposed teeth as they protrude inwardly and leave a limited amount of space inbetween. Smaller material is caught between the root of each tooth 58 and the tube 40 itself as the tooth is broader at that end and a natural pocket is formed. The teeth 58 may be spaced at equal or intermitted intervals throughout the tube. The variation of this embodiment is shown in FIGS. 27–29 wherein the size of the teeth 58 become progressively larger in volume and proportion permitting the material to be retained at different intervals preventing clogging of the ejector in one area prematurely.

A second embodiment of the retaining means is depicted in FIGS. 30 and 31 where fingers 60 are used to catch and retain the debris. This embodiment functions in the same manner, however the shape is slightly different providing greater width at the ends and the shape and angle relative to the tube internal wall.

A third embodiment illustrated in FIGS. 32 and 33 again functions in the same manner except shelves 62 and employed for catching the debris. These shelves 62 are formed at an acute angle, relative to the flow, and are rectangular in shape.

It should be noted that the second and third embodiment of the retaining means may also be progressively larger in size from the first end to the second end of the tube.

A fourth embodiment of the retaining means is a trap 64 formed integrally with the tube 40. Within the trap may also be included a plurality of teeth 60 as shown in FIG. 34. Thus, the combination of gravity and reduced suction negative pressure retain the debris in the bottom of the tube interior at the lowest point in the trap. This trap 64 may be formed in the shape of a loop 66 as shown in FIG. 34 or a 68 as illustrated in FIG. 35, either configuration working equally well. Again, as the debris is trapped and retained by the reduced area of the bend, the entire ejector is discarded after use and unless excessive work is accomplished on the patient there is sufficient capacity for a single procedure.

Figure 1:
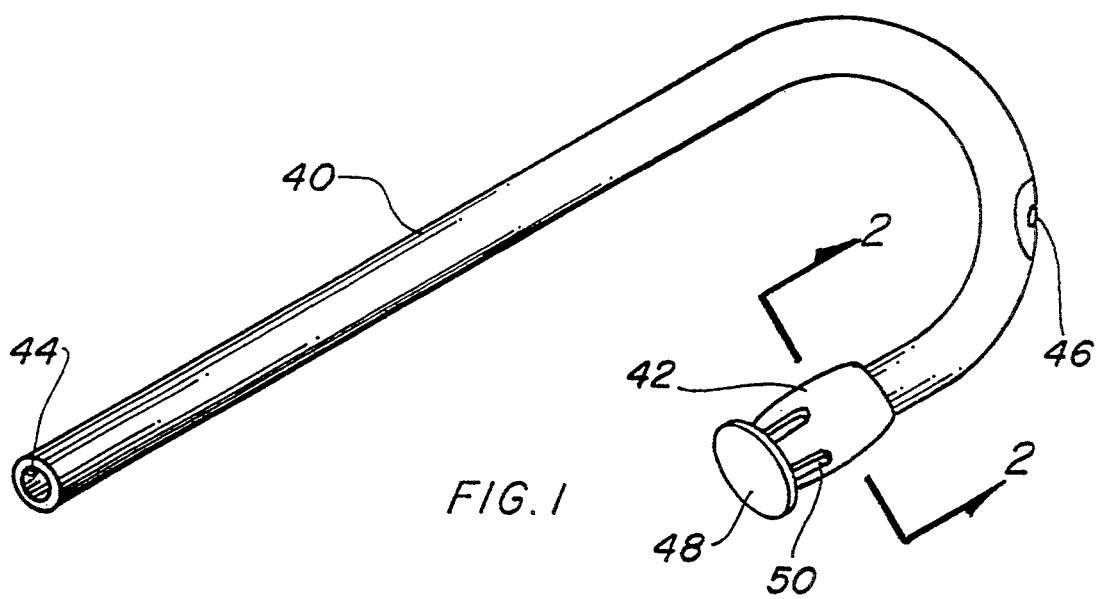
FIG. 1 is a partial isometric view of the preferred embodiment.
Figure 2:
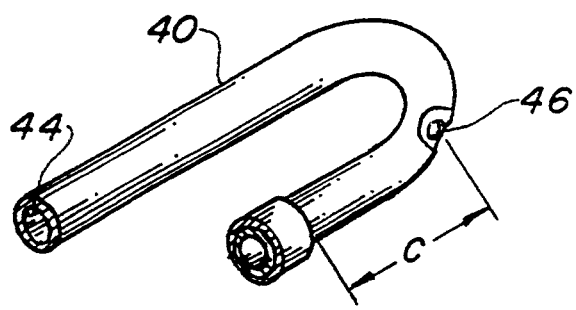
FIG. 2 is a cross sectional view taken along lines 1—1 rotated 15° counterclockwise, illustrating the junction of the tube inside the tip and the location of the beveled hole.
Figure 3:
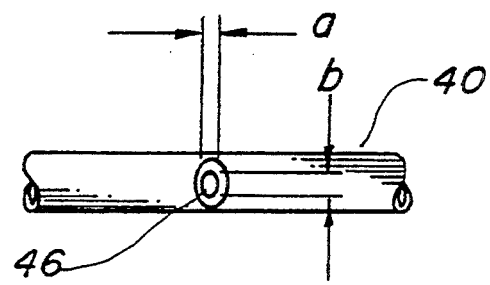
FIG. 3 is an end view of the tube with the hole stretched partially closed.

In operation the tube is bent to the desired U-shape as illustrated in FIG. 1 and the ejector is placed in the patient's mouth and is held by the shape with the bend intersecting the patient's front teeth for support. The dental practitioner uses the beveled hole to both clean tools as shown in FIGS. 8–11 and to control volume as depicted in FIG. 14. At the end of the dental procedure, the entire ejector with its retained debris is discarded.

While the invention has been described in complete detail and pictorially shown in the accompanying drawings, it is not to be limited to such details, since many changes and modifications may be made in the invention without departing from the spirit and scope thereof, hence, it is described to cover any and all modifications and forms which may come within the language and scope of the claims.

I claim:

1. A disposable saliva ejector comprising:
    a formable hollow tube having a first end and a second end, with the first end having a tip with openings therein for drawing in saliva and the second end for connection to a vacuum source,
    said tube having a beveled hole therein,
    said hole further comprises a concave dish like surface on the tube exterior with the hole penetrating the tube at a sharp angle permitting dental tools to be inserted into the hole without binding on the tube exterior and jointly permitting a dental practitioner to place a finger over the hole for vacuum regulation,
    said tip having a tip guard integrally formed therewith to prevent tissue aspiration from a patient into the openings of the tip, and
    debris retaining means within the formable hollow tube positioned such that waste materials and tartar are retained therein for disposal when use of the saliva ejector is completed on a singular patient.

2. The saliva ejector as recited in claim 1 wherein said hole having a diameter of from 2 to 4 millimeters when the tube is straight.

3. The saliva ejector as recited in claim 1 wherein said beveled hole further comprises an oval shape deformed as the tube is bent into an arc reducing the cross sectional area for providing adjustable flow and negative pressure characteristics within the tube.

4. The saliva ejector as recited in claim 1 further comprising said beveled hole is located from 9 to 35 millimeters from the tip of the formable tube to the hole center.

5. The saliva ejector as recited in claim 1 wherein said tip guard further comprises a flat pad on a distal end thereof with the entire tip guard disposed over the first end of the tube.

6. The saliva ejector as recited in claim 5 further comprises an air cushion integrally formed on a distal end of the pad making the pad pliable and soft where it is in contact with delicate tissues and mucous membrane in a patient's mouth.

7. The saliva ejector as recited in claim 5 further comprises a closed cell sponge integrally formed on a distal end of the pad making the pad pliable and soft where it is in contact with delicate tissues and mucous membrane in a patient's mouth.

8. The saliva ejector as recited in claim 1 wherein said tip guard further comprises a flat pad on a distal end thereof with the entire tip guard disposed within the first end of the tube.

9. The saliva ejector as recited in claim 8 further comprising a soft resilient material integrally formed on a distal end of the pad making the pad pliable and soft where it is in contact with delicate tissues and mucous membrane in a patient's mouth.

10. The saliva ejector as recited in claim 8 further comprising an air cushion integrally formed on a distal end of the pad making the pad pliable and soft where it is in contact with delicate tissues and mucous membrane in a patient's mouth.

11. The saliva ejector as recited in claim 8 further comprising a closed cell sponge integrally formed on a distal end of the pad making the pad pliable and soft where it is in contact with delicate tissues and mucous membrane in a patient's mouth.

12. The saliva ejector as recited in claim 1 wherein said debris retaining means further comprises a plurality of triangular shaped teeth disposed at intervals inside the tube facing inwardly forming traps as the debris flows by retaining larger objects between opposed ends and smaller material between the teeth and the tube.

13. The saliva ejector as recited in claim 12 further comprising said teeth becoming progressively larger in size from the first to the second end of the tube for gradually retaining debris of a varied size on and between the teeth.

14. The saliva ejector as recited in claim 1 wherein said debris retaining means further comprises a plurality of fingers disposed at intervals inside the tube facing inwardly forming traps as the debris flows by retaining larger objects between opposed ends and smaller material between the fingers and the tube.

15. The saliva ejector as recited in claim 1 wherein said debris retaining means further comprises a plurality of shelves disposed at intervals inside the tube facing inwardly forming traps as the debris flows by retaining larger objects between opposed ends and smaller material between the shelves and the tube.

16. The saliva ejector as recited in claim 15 further comprising a loop formed into the hollow tube.

17. The saliva ejector as recited in claim 15 further comprising a S-bend formed into the hollow tube.

18. The saliva ejector as recited in claim 1 wherein said debris retaining means further comprises a trap formed integrally with the hollow tube such that gravity and reduced suction negative pressure retain debris in the tube interior at the trap.

19. The saliva ejector as recited in claim 1 wherein said tools include both single-integral instruments and rotary instruments.

* * * * *